United States Patent [19]

Murch et al.

[11] Patent Number: 5,849,678
[45] Date of Patent: *Dec. 15, 1998

[54] CLEANING/SANITIZING METHODS, COMPOSITIONS AND/OR ARTICLES FOR PRODUCE

[75] Inventors: Bruce Prentiss Murch, Gosforth, United Kingdom; Brian Joseph Roselle, Fairfield, Ohio; Kyle David Jones, West Chester, Ohio; Keith Homer Baker, Cincinnati, Ohio; Thomas Edward Ward, Oxford, Ohio; Toan Trinh, Maineville, Ohio

[73] Assignee: The Procter & Gamble Company, Cincinnati, Ohio

[ * ] Notice: The term of this patent shall not extend beyond the expiration date of Pat. No. 5,500,143.

[21] Appl. No.: 833,552

[22] Filed: Apr. 7, 1997

Related U.S. Application Data

[62] Division of Ser. No. 495,286, Jun. 27, 1995.

[51] Int. Cl.$^6$ ....................................................... C11D 9/00
[52] U.S. Cl. .......................... 510/111; 510/370; 510/371; 510/382; 510/383; 510/405; 510/407; 510/413; 510/421; 510/422; 510/434; 510/437; 134/25.3; 134/16; 134/25.1; 134/40; 426/335
[58] Field of Search ................................. 510/111, 370, 510/371, 382, 383, 405, 407, 413, 421, 422, 434, 437; 8/137; 134/25.3, 16, 251.1, 40; 426/335

[56] References Cited

U.S. PATENT DOCUMENTS

| | | | |
|---|---|---|---|
| 2,472,794 | 6/1949 | Cothran | 99/156 |
| 3,857,983 | 12/1974 | Roth | 426/287 |
| 3,920,856 | 11/1975 | Aepli et al. | 426/287 |
| 4,002,579 | 1/1977 | Mizutani et al. | |
| 4,140,649 | 2/1979 | Bossert et al. | |
| 4,177,294 | 12/1979 | Lehmann et al. | 426/271 |
| 4,244,975 | 1/1981 | Herbst et al. | 426/271 |
| 4,259,216 | 3/1981 | Miyajima et al. | |
| 4,287,102 | 9/1981 | Miyaajima et al | |
| 4,414,128 | 11/1983 | Goffinet | |
| 4,698,181 | 10/1987 | Lewis | 510/340 |
| 4,808,330 | 2/1989 | Chung | |
| 5,075,026 | 12/1991 | Loth et al. | |
| 5,094,868 | 3/1992 | Wolfram et al. | 426/286 |
| 5,190,747 | 3/1993 | Sekiguchi et al. | 424/56 |
| 5,306,444 | 4/1994 | Kitamura et al. | |
| 5,320,772 | 6/1994 | Tricca | 15/104.93 |
| 5,342,630 | 8/1994 | Jones | 424/717 |
| 5,350,541 | 9/1994 | Michael et al. | 510/437 |
| 5,366,995 | 11/1994 | Savage et al. | 514/588 |
| 5,498,295 | 3/1996 | Murch et al. | 143/16 |
| 5,500,048 | 3/1996 | Murch et al. | 143/6 |
| 5,500,143 | 3/1996 | Murch et al. | 510/111 |
| 5,503,764 | 4/1996 | Murch et al. | 510/111 |
| 5,549,758 | 8/1996 | Murch et al. | 134/6 |

FOREIGN PATENT DOCUMENTS 4023418  2/1992  Germany .

OTHER PUBLICATIONS

English translation of DE 4,023,418 A1. Feb. 1992.
Code of Federal Regulations, Food and Drugs, §173.315, "Chemicals used in wasing or to assist in the lye peeling of fruits and vegetables". (Date Unknown).

*Primary Examiner*—Alan Diamond
*Attorney, Agent, or Firm*—Robert B. Aylor

[57] ABSTRACT

Basic cleaning compositions using toxicologically-acceptable ingredients for cleaning fruits and vegetables are provided. Liquid formulations comprising detergent surfactant, such as oleate, alcohol ethoxylates, etc., and neutralized phosphoric acid are sprayed onto apples, lettuce and the like to remove soil and unwanted deposits, especially wax. Articles for applying the compositions to produce by spraying are disclosed. Use of the compositions for disinfectancy/sanitization of produce and cleaning/disinfectancy/sanitization of non-food inantimate surfaces are disclosed.

5 Claims, No Drawings

5,849,678

CLEANING/SANITIZING METHODS, COMPOSITIONS AND/OR ARTICLES FOR PRODUCE

This is a division of application Ser. No. 08/495,286, filed on Jun. 27, 1995.

TECHNICAL FIELD

The present invention relates to methods for removing dirt and other unwanted residues from produce, e.g., fruits and vegetables, which is intended for ingestion by humans or lower animals and to detersive compositions, especially in liquid form, which are especially suitable for practicing said methods.

BACKGROUND OF THE INVENTION

It is well-known and appreciated by consumers that fruits and vegetables should be thoroughly washed prior to ingestion in order to remove soils and other unwanted residues which may be undesirably clinging to the surfaces thereof In addition, some consumers wish to remove the artificial "waxy" coatings which may be applied to some fruits to retard moisture loss for increased storage life and to enhance their appearance. It has been estimated that 95% of consumers recognize the need for thorough washing but, ordinarily, only use tap water for this purpose. On the order of 5% of those consumers who do wash their vegetables use a household cleaner, typically a liquid dishwashing product, to help ensure cleanliness. However, dishwashing products are not specifically intended for such use, inasmuch as they are usually designed to provide high, persistent suds which makes them inconvenient to remove from the fruits or vegetables which have been washed therewith. It will also be appreciated that the formulation of truly effective compositions, especially those which can be used safely by individual consumers, for washing fruits and vegetables presents a unique problem to the formulator, inasmuch as many art-disclosed cleaning ingredients would, presumably, not be desirable for use in direct contact with foods where they might not be fully removed.

Moreover, it would be especially desirable to provide effective, toxicologically-acceptable cleaning compositions for fruits and vegetables in the form of substantially low-sudsing liquid solutions which are clear or which have only minimal haziness. Liquid solutions are convenient for the user, since they can be applied directly to soiled fruits and vegetables, followed by rinsing in tap water. The clarity of the liquids connotes cleanliness to the user and is thus highly desirable. Low sudsing is an important attribute so that removal of the solution by rinsing is achieved quickly and easily. It would also be of advantage if such compositions could be provided in the form of concentrates, which could be diluted by the consumer before use and/or applied to the fruits and vegetables as a direct spray-on.

Unfortunately, many toxicologically-acceptable cleaning ingredients do not meet the aforesaid requirements for clear, low-sudsing, dilutable liquid products. Many detersive surfactants form cloudy or even opaque suspensions, even in soft water. Of course, many surfactants are specifically designed to be high sudsing. Still others form relatively intractable phases in their concentrated form.

It has been disclosed that soap and/or certain nonionic surfactants, properly formulated, e.g., with water-soluble oleate or laurate salts and other ingredients can provide liquid compositions having the desired properties described above. It has also been disclosed that preferred compositions can be formulated in the basic pH range. Even when such basic compositions do have a soapy feel, they are preferred over the acidic compositions herein for removing artificial waxy coatings, especially from fruit such as apples. However, the invention also comprises basic compositions having less soapy feel. It has now been discovered that the addition of neutralized phosphoric acid provides even better cleaning, especially of waxy material, even at the same pH.

BACKGROUND ART

The use and selection of cleaning ingredients for the purpose of washing fruits and vegetables is described by the United States Code of Federal Regulations, Title 21, Section 173.315: "Ingredients for use in washing or lye peeling of fruits and vegetables". These regulations restrict the ingredients that may be used for direct contact with food to those described as "generally regarded as safe" (GRAS), and a few other selected ingredients. These sections also provide certain limitations on the amount of material that can be used in a given context.

Among these ingredients, the experienced formulator will find only a few ingredients which can provide effective cleaning of hydrophobic residues, such as waxes, oils, or man-made chemical residues such as pesticides. It is recognized these types of residues are removed most readily by surface active ingredients in water, or by organic solvents largely in the absence of water. Other types of soils, especially particulate insoluble soils that do not readily disperse in water, are effectively removed by surface active materials in water, especially when aided by complex anionic salts, such as citrates (polycarboxylates), or polyphosphate salts.

Within this limited group of ingredients the range of effective cleaning compositions well suited to the task of cleaning fruits and vegetables, especially as practiced by individual consumers, have not been previously described. It is desirable to formulate liquid compositions which are amenable to either direct application to produce, preferably by spray application, or could be provided in suitable concentrated form to allow convenient dilution in a bowl or sink of water for washing of produce by immersion. Further, it is desirable if the compositions are low sudsing, and easily rinsed, without leaving residue. Preferred compositions should be mild to the hands, especially for direct application.

*Food Chemical News. Inc.,* 1991, p. 334.1, reports that PEG 200–9500 has been cleared under §178.3750 as a component in articles for use in contact with food (*Fed. Register*, Oct. 15, 1968). Nonetheless, for washing produce, polyethylene glycol should be affirmed as GRAS.

SUMMARY OF THE INVENTION

The present invention encompasses methods for cleaning produce, especially fruits and vegetables, (and compositions, as disclosed hereinafter, for practicing said methods) at a basic pH. The present invention comprises several aspects including:

I. A method for cleaning produce comprising contacting the surfaces of said produce by direct application of an aqueous cleaning solution typically comprising:
  (a) from about 0.01% to about 15% of $C_8$–$C_{18}$ fatty acid;
  (b) optionally, from about 0.1% to about 4% by weight of nonionic surfactant, especially ethoxylated and/or propoxylated adducts of aliphatic $C_{12-18}$ alcohols, but preferably less than about one eighth of the amount of said fatty acid;
  (c) optionally, from about 0.1% to about 4% by weight of organic polycarboxylic acid, preferably citric acid;

(d) optionally, up to about 0.2% by weight of base-stable anionic surfactant such as the alkali or alkaline earth salts of dodecylbenzene sulfonate;

(e) optionally, toxicologically-acceptable basic buffer such as potassium and/or sodium basic materials, e.g., the hydroxides and/or salts of carbonate and/or bicarbonate;

(f) optionally, toxicologically-acceptable preservative;

(g) optionally, but preferably, from about 0.05% to about 10%, preferably from about 0.1% to about 5%, more preferably from about 0.3% to about 2% of phosphoric acid;

(h) optionally, at least about 0.05%, preferably from about 0.1% to about 10%, most preferably from about 0.25% to about 3.0%, by weight, of water-soluble polyethylene glycol having a molecular weight of about 200, or higher; and (i) the balance comprising an aqueous carrier selected from water and, optionally, low molecular weight, toxicologically-acceptable organic solvent such as ethanol, glycerol, etc.;

all of the acidic materials above being, of course, neutralized under the alkaline conditions of the product, preferably neutralized with sodium and/or potassium, preferably potassium, compatible basic material, wherein said aqueous solution has a pH in the range of 9.5 or greater, preferably more than about 11, and even more preferably from about 11.5 to about 12.5, and said composition preferably being essentially free of any material that is not toxicologically acceptable.

The inventions disclosed herein preferably encompass compositions for use in a method for cleaning fruits and vegetables at a basic pH above about 9.5, comprising:

(a) from about 0.01% to about 15% of $C_8$–$C_{18}$ fatty acid which is neutralized, preferably a member selected from the group consisting of sodium or potassium oleate (preferred), or from about 0.5% to 10% by 9at E weight of sodium or potassium laurate;

(b) optionally, from about 0.1% to about 4% by weight of nonionic surfactant, especially ethoxylated/propoxylated adducts of aliphatic $C_{12-18}$ alcohols, but preferably less than about one eighth of the amount of said fatty acid;

(c) optionally, but preferably, from about 0.2% to about 4% by weight of potassium and/or sodium polycarboxylate, having detergent building capability and preferably being derived from natural sources, such as potassium and/or sodium citrate, as a dispersant for particulate soils;

(d) optionally, up to about 0.2% by weight of base-stable anionic surfactant such as the alkali or alkaline earth salts of dodecylbenzene sulfonate;

(e) optionally, toxicologically-acceptable basic buffer such as potassium and/or sodium basic materials, e.g., the hydroxides and/or salts of carbonate and/or bicarbonate;

(f) optionally, toxicologically-acceptable preservative;

(g) optionally, but preferably, from about 0.05% to about 10%, preferably from about 0.1% to about 5%, more preferably from about 0.3% to about 2% of phosphoric acid; and (h) optionally, at least about 0.05%, preferably from about 0.1% to about 10%, most preferably from about 0.25% to about 3.0%, by weight, of water-soluble polyethylene glycol having a molecular weight of about 200, or higher;

(i) the balance preferably comprising aqueous carrier selected from water and, optionally, low molecular weight, toxicologically-acceptable organic solvent such as ethanol, glycerol, etc., preferably selected from water and water-ethanol;

wherein said aqueous cleaning solution has a pH of 9.5 or greater, and preferably employs carbonate salt, or salts, as buffer (e), preferably with hydroxide base, to provide a pH of from about 11 to about 12.5, more preferably from about 11.5 to about 12.5. The compositions can also be formulated as concentrates, in which at least part of (i) is removed and the levels of the remaining ingredients are adjusted to complete the formula. In all of the above lists of components, if an ingredient can be classified in more than one place, it will be classified in the first place it can appear.

A more specific method for cleaning fruits and vegetables at a basic pH, preferably more than about 9.5, comprises contacting the surfaces of said fruits and vegetables with an aqueous cleaning solution comprising potassium oleate, preferably at a level of more than about 0.5%. Potassium oleate is mild, rinses well, has minimal odor, is effective in removing unwanted materials, especially wax, from apples, does not oversuds, and is very safe, even when the composition is misused and the vegetable, or fruit, etc., is not completely rinsed. Therefore, it is a uniquely preferred surfactant for use in cleaning food materials like vegetables and fruits. The potassium cation is more useful than the sodium cation, especially in the absence of polyethylene glycol, since the potassium oleate is quite soluble whereas the sodium oleate tends to form a less soluble soap, especially at low temperatures.

A concentrated, alkaline method for cleaning produce comprises contacting the surfaces of produce with a cleaning solution containing from about 0.5% to about 15%, preferably from about 0.75% to about 8%, more preferably from about 1% to about 5%, detergent surfactant, preferably one that is GRAS, and more preferably said oleate surfactant, said cleaning solution having a pH of from about 9.5 to about 12.5, preferably from about 11 to about 12.5, especially when the detergent surfactant is a soap such as the said oleate, more preferably from about 11.5 to about 12.3. Such compositions when used in an effective amount to clean apples coated with wax, will provide more effective removal of the wax when combined with the neutralized phosphoric acid. Removal of wax from apples is one of the most difficult cleaning tasks and therefore is indicative of overall superior performance. It is important to remove as much wax as possible to minimize the amount of any undesirable materials that may be trapped by the wax.

Another preferred variation in the above methods for cleaning produce involves placing said cleaning solutions in a spray container to provide a spray of said solution to distribute the said solution, or solutions, over the surfaces of the produce while utilizing only a minimum amount of the cleaning solution and minimizing the exposure of the remaining solution to the atmosphere, where the solution is more likely to be contaminated and/or exposed to oxygen, both of which tend to cause undesirable changes in the solutions from aesthetic and/or performance considerations. In such spray processes, there is only need for a relatively small amount of material in the package, and for individual consumer use, this is desirable, since some consumers will not be able to manipulate large weights. For individual consumer usage, typically, the container will contain no more than about two gallons (about eight liters), preferably no more than about one gallon (about four liters), especially when the container is a spray container, even one that has a tube that permits the spray device to be manipulated while the bulk container remains in place. More preferably such spray containers contain about one liter, or less, of cleaning solution.

The invention encompasses basic cleaning compositions in both concentrated and dilute forms, especially adapted for practicing said methods. (In the following disclosure, the lower amounts of the specified ingredients denote the dilute forms of the compositions herein and the higher amounts denote the concentrated forms which are typically diluted by a factor of from about 2 to about 3.) The compositions can be concentrated even more to non-aqueous liquids or solids according to the teaching in U.S. Pat. No. 5,280,042, Lopes, said patent being incorporated by reference. Such compositions include the following.

A composition for cleaning fruits and vegetables at a basic pH, comprising:
 (a) from about 0.1% to about 15%, preferably from about 1% to about 5%, by weight of a member selected from the group consisting of sodium or potassium oleate (preferred), sodium or potassium laurate, or mixtures thereof;
 (b) optionally, from about 0.1% to about 4%, preferably about 0.3% to about 1.0%, by weight of nonionic surfactant as described above;
 (c) from about 0.2% to about 4% by weight of polycarboxylic acid salt, especially potassium hydrogen citrate;
 (d) from about 0.3% to about 5% of ortho-phosphoric acid; and
 (e) the balance comprising aqueous carrier selected from water and water-ethanol;
wherein said composition has a pH of 9.5 or greater.

Preferably, the basic compositions herein contain from about 0.5% to about 1.5% by weight of potassium, and/or sodium, carbonate and/or bicarbonate buffer and have a pH of from about 11.5 to about 12.5.

Preferred compositions for use herein in a concentrated alkaline method contain from about 0.1% to about 15%, preferably from about 0.5% to about 8%, more preferably from about 1% to about 5%, detergent surfactant, preferably one that is GRAS; from about 0.3% to about 5% of ortho-phosphoric acid and have a pH of from about 9.5 to about 12.5, preferably from about 11.5 to about 12.3. Such compositions, when used in an effective amount to clean apples coated with wax, will provide more effective removal of the wax. Removal of wax from apples is one of the most difficult cleaning tasks and therefore is indicative of overall superior performance.

The present invention also encompasses detersive compositions with an improved tactile impression which are especially adapted for cleaning fruits and vegetables, comprising:
 (a) at least about 0.1%, preferably from about 0.5% to about 8%, most preferably from about 1% to about 5%, by weight, of a $C_{12}$–$C_{18}$ fatty acid or salt thereof;
 (b) at least about 0.05%, preferably from about 0.1% to about 10%, most preferably from about 0.25% to about 3.0%, by weight, of water-soluble polyethylene glycol having a molecular weight of about 200, or higher;
 (c) from about 0.1% to about 5% of neutralized ortho-phosphoric acid; and
 (d) water or water-ethanol fluid carrier, said composition having a basic pH.

The balance of the composition can comprise various optional adjunct materials, pH-adjusting agents, perfumes or essences, preservatives and the like.

In a preferred mode, component (b) has a molecular weight in the range from about 300 to about 9500.

Typical compositions herein are wherein component (a) is potassium oleate, and wherein the weight ratio of (a):(b) is in the range from about 1:2 to about 30:1, preferably from about 1:1 to about 15:1.

The compositions having improved tactile impression are typically formulated in the basic pH range, preferably from about pH 9.5 to about pH 12.5. Preferred compositions have a viscosity at room temperature of less than about 100 centipoise, preferably less than about 50 centipoise for sprayable compositions.

Preferred compositions for use herein contain only materials that are GRAS, including, of course, direct food additives affirmed as GRAS, to protect against possible misuse by the consumer. Traditionally, most suggestions for cleaning of fruits and/or vegetables have contemplated a commercial scale where there is typically more control over the conditions, especially the amount and thoroughness of rinsing. The present invention, especially the methods involving use of hand held trigger activated spray means are primarily/solely suitable for use by individual consumers so that it is essential that extra safety be built into the product. Failure to rinse thoroughly after cleaning is less of a concern if all of the ingredients are GRAS. This is especially important when concentrated basic compositions suitable for removal of wax from apples are used. The larger amounts of materials needed for removal of wax create an heretofore unknown level of risk for the individual consumers, many of whom are not likely to read, or follow, instructions which would permit safe use of non-GRAS materials.

The ingredients in the above compositions are preferably selected and used in proportions which provide substantially clear compositions. "Substantially clear" includes only minimal haziness, and preferably the compositions are completely clear. The ingredients are also selected to have minimal odor, both initially and after storage. The lack of odor is especially important in compositions for use on food. The compositions preferably have a viscosity that is more than about 2 centipoise, preferably more than about 10 centipoise when at rest, but thin under shear to permit easy dispensing, especially from spray containers.

Below pH about 9.7, the compositions can exhibit some objectionable fatty acid odor. Even at the optimal pH's above 11, some odor can persist. In order to mask this odor, the compositions can contain a GRAS perfume, or essence, ingredient. Especially preferred for this use are oils derived from citrus fruit, e.g., oranges, lemons, limes, grapefruits, tangerines, tangelos, etc. which contain relatively large amounts of terpenes.

All documents cited herein are incorporated herein by reference.

DETAILED DESCRIPTION OF THE INVENTION

The following toxicologically-acceptable ingredients are used in the preparation of the preferred compositions herein. By "toxicologically-acceptable" is meant that any residues from the ingredients of the compositions which may remain on the fruits or vegetables cleansed therewith are safe for ingestion by humans and/or lower animals.

Nonionic Surfactant—The nonionic surfactant is preferably selected from materials known in the art, such as alkylene oxide (ethylene oxide and/or propylene oxide) adducts of $C_{10-18}$ aliphatic alcohols or acids, $C_{10-18}$ aliphatic alcohol adducts of glucose (alkyl polyglucosides). The specific nonionic surfactant selected ideally has a hydrophilic-lipophilic balance (HLB) greater than about 10, and a cloud point above about 35° C. in the composition. The United States Code of Federal Regulations (CFR) specifically describes an ethylene oxide/propylene oxide adduct of C12–18 aliphatic alcohol of molecular weight of about 800. Such a material is available as PLURAFAC RA-20 (BASF).

In the basic compositions containing soap, the alkoxylated alcohol functions mainly as a dispersant for any soap curd which may form during the cleansing operation. Further, it is recognized that the selection of non-nitrogen containing nonionics can minimize the possibility of microbial growth in the dilute surfactant compositions.

Fatty Acid and/or Salts Thereof—The acidic compositions herein are preferably formulated using an unsaturated fatty acid; oleic acid is preferred and convenient for this use. However, the particular oleic acid that is selected should preferably be low in polyunsaturates, e.g., contain less than about 10%, preferably less than about 7%, more preferably less than about 5%, polyunsaturated acid minor components, and will typically have an Iodine Value (IV) of from about 70 to about 100, preferably from about 83 to about 95, more preferably from about 85 to about 90. Polyunsaturated fatty acids are not preferred herein, due to odor problems. However, this is primarily from aesthetic considerations since such acids are effective in cleaning. The amount of polyunsaturated fatty acids should be less than about 8%, preferably 0%. The amount of polyunsaturated fatty acids with more than about two double bonds should be less than about 1%, preferably 0%. Saturated fatty acids are unacceptable as they have limited solubility for longer chain-length materials ($\geq C_{12}$), or have unacceptable odor ($\leq C_{10}$). For example, stearic and/or tallow fatty acids soaps, even potassium soaps, do not have enough solubility at room temperature, where most produce cleaning is done by individual consumers, to formulate even compositions containing the minimum of about 0.1% soap required for acceptable cleaning. Other specific solubilizing surfactants in higher proportions would be required to solubilize these saturated fatty acids. Pamolyn 100 FGK oleic acid is a good example of a suitable commercial fatty acid.

Phosphoric Acid

Phosphoric acid is an extremely desirable component for improving the removal of, e.g., wax from apples. The advantage is not due solely to pH since the improvement is observed at any pH. E.g., as disclosed hereinafter, when the pH is varied from about 11 to about 12, the results are superior when the neutralized ortho-phosphoric acid is present. The result is also not due to any ability of the neutralized phosphoric acid to act as a builder to inhibit the problems associated with water hardness, since the results are improved when the compositions are used fill strength by application directly on the waxed surface.

It is surprising that the neutralized orthophosphoric acid provides such a large benefit. The advantage is especially noticed when the compositions are used full strength, e.g., by spraying the composition directly onto the surface of the produce.

Polyethylene Glycol—The water-soluble polyethylene glycol polymer (PEG) employed herein is the known article of commerce and is available under a variety of trade names, of which CARBOWAX (Union Carbide Corporation) is exemplary. PEG's in the average molecular weight range of from about 200 to about 20,000 can be used herein, and PEG as CARBOWAX in the average molecular weight range of at least about 200, typically 300 to about 9500, is convenient and preferred. As disclosed above, the compositions herein will comprise at least about 0.05%, by weight, of the PEG and will typically comprise from about 0.1% to about 10%, by weight, of PEG. The amounts used can vary with the molecular weight of the PEG, the amount of oleate or other fatty acid used in the composition, the desired viscosity of the composition, and like factors within the discretion of the formulator. The following Table 1 illustrates the variation in viscosity which can be effected using various levels of PEG and varying PEG molecular weights in a liquid composition (Control) comprising 3% potassium oleate. Table 1 also illustrates the effect of sodium benzoate (Bz) on viscosity.

TABLE I

| Composition | Viscosity (cP* as made) | |
|---|---|---|
|  | 72° F. (22° C.) | 43° F. (6° C.) |
| Control (no PEG) | 7 | 110 |
| Control + 0.674% Bz | 23 | 1000 |
| Control + 0.118% Bz | 7 | 159 |
| Control + 0.1% PEG 400 | 5 | 36 |
| Control + 0.5% PEG 400 | 2 | 17 |
| Control + 0.1% PEG 8000 | 5 | 23 |
| Control + 0.5% PEG 8000 | 8 | 4 |

*Viscosity in centipoise as measured using Brookfield LVTD #2 spindle, 60 rpm at the designated temperature.

In a typical mode, the preferred compositions herein that have an improved tactile impression will comprise oleate-:PEG weight ratios in the range from about 1:2 to about 30:1, preferably from about 1:1 to about 15:1.

Tactile Impression—The compositions herein which contain the polyethylene glycol are characterized not only by their excellent cleaning performance and sudsing/rinsability properties, but also by their improved viscosity properties and improved "feel". While, as disclosed above, the improved viscosities of the compositions herein are readily demonstrated quantitatively using standard measurement techniques, the improved feel of the compositions which come into contact with the users' hands is a qualitative tactile impression. However, this improved, "non-slippery", "non-soapy" improvement in skin feel can be demonstrated by rubbing Test (PEG-containing) and Control (no PEG) compositions on the hands or inner forearms of volunteer graders. Even in such rudimentary tests, the graders can readily distinguish the improved tactile impression of the compositions made in accordance with this invention.

Optional Surfactants—Optionally, base stable anionic surfactants can be employed, as allowed by the United States Code of Federal Regulations, Title 21, Section 173.315. Preferred are salts of dodecylbenzene sulfonate, typically at levels up to 0.2%. Also described in the CFR are phosphate esters of ethylene and/or ethylene/propylene oxide adducts of aliphatic alcohols, dioctyl sulfosuccinate, and 2-ethylhexyl sulfate.

Sequestrant/builder—The organic polycarboxylic acid, or salt thereof, e.g., citric acid, or sodium and/or potassium citrate, and/or ethylenediaminetetraacetic acid, or sodium and/or potassium ethylenediaminetetraacetate, are standard items of commerce and are GRAS. Other organic poly carboxylic acids, especially those that are GRAS, such as tartaric, malic, etc. acids, can also be used. When formulating the basic formulations herein, it is preferred to use the potassium salt, as compared with the sodium salt, to provide ease of formulatability. Complex phosphates can also be used, but are generally avoided due to regulatory considerations.

Buffer—Toxicologically-acceptable basic buffers can be used in the compositions herein to maintain product pH in the base range. For ease of formulatability, it is highly preferred that such basic buffers be in their potassium salt form. Potassium citrate is a preferred dispersant for particulate soils. Potassium carbonate is a convenient and preferred basic pH buffer. Sodium bicarbonate is a highly desirable material to add to the compositions of this invention as a part of the buffering system since it is readily available as baking soda in food grade and is therefore relatively inexpensive, while providing a highly desirable purity to the composition. Compositions formulated with a mixture of potassium and sodium cations in molar ratios of from about 1:1 to about 10:1, preferably from about 2:1 to about 8:1, more preferably from about 4:1 to about 5:1 potassium to sodium, e.g., as provided by mixtures of potassium hydroxide (hydrate) and sodium bicarbonate, have desirable rheological properties. The compositions are sufficiently viscous, so as to cling to the fruit or vegetable until spread, but are readily dispensed, e.g, by means of a spray device, either aerosol or finger-activated pump. The levels and identities of the ingredients are adjusted to provide products having the desired viscosities as set forth herein, e.g., more than about 2, preferably more than about 5, more preferably more than about 10 centipoise when at rest, and less than about 150, preferably less than about 100, more preferably less than about 50 centipoise under shear of $\geq \sim 1000$ sec$^{-1}$.

The ability of the preferred compositions containing mixtures of both sodium and potassium cations to shear thin is important to promote easy dispensing, especially when the compositions are sprayed, while maintaining the ability to be thick, cling, and delay run off after being applied to the produce.

The pH is preferably not greater than about 12.5, and especially does not contain large amounts of buffer at higher pHs for consumer safety, especially when the compositions are sprayed.

Preservative—Formulating the present compositions at high pH reduces the tendency for biological growth of contaminants, such as bacteria, fungi, or molds. At neutral PH, an increased reliance on preservatives is required to insure the lack of biological growth through contamination in making or in use. Standard food-grade preservatives such as ethylenediaminetetraacetic acid and/or the salts thereof, at a level of from about 0.01% to about 0.2% of ethylenediaminetetraacetic acid, or its sodium and/or potassium salts, can be used although, in general, the basic pH compositions herein do not require a preservative.

Antioxidants The use of commercial oleic acid, or oleate salts, can be complicated by development of off-odors and/or yellowing of the compositions in which they appear. These undesirable properties are believed to be caused by complex side reactions initiated by the reaction of oxygen with primarily the polyunsaturated components of the fatty acid stock. These results can be avoided, or minimized, by avoiding contact with air, or by controlling the quality of the fatty acid stock so that the amount and type of polyunsaturates are minimized as described above, and/or by the addition of antioxidants.

It has been found, that the addition of tocopherols (e.g., Vitamin E, or tocopherol acetates) in alkaline formulations is advantageous, as they do not degrade, nor do they impart a strong color. They inhibit the development of off-odors for extended periods of time so that the need for masking scents is minimized, or eliminated, particularly for oleic acid stocks of high quality, as described above. The use of butylated phenols, such as BHT and BHA is also useful, but the quantity should be limited to avoid imparting colors to the compositions. Other food grade antioxidants such as Vitamin C and sulfites, are desirable to prevent deterioration of the compositions by the action of oxygen, but care must be taken since vitamin C can suffer color degradation and sulfites can cause odor problems. Sulfites also have been the target of potential health concerns.

Fluid Carrier—The major proportion, e.g., more than about two thirds, (typically, 80%–98%, by weight) of the compositions herein comprises water as the solubilizing carrier for the ingredients. As noted in the Examples hereinafter, water-ethanol can also be employed and is especially preferred when formulating the basic pH compositions herein. The ethanol level preferably should not exceed 2% in the solution used to clean the produce, to avoid an alcoholic odor, especially when spraying. Other compatible, water-soluble, low molecular weight solvents such as glycerol can also be used.

The compositions herein are preferably used by placing them in a package comprising either an aerosol container or a non-aerosol spray device "spray means." Said spray means is any of the manually activated, preferably "trigger-type," means for producing a spray of liquid droplets as is known in the art. Typical spray means are disclosed in U.S. Pat. Nos.: 4,082,223, Nozawa, issued Apr. 4, 1978; 4,161,288, McKinney, issued Jul. 17, 1979; 4558,821, Tada et al., issued Dec. 17, 1985; 4,434,917, Saito et al., issued Mar. 6, 1984; and 4,819,835, Tasaki, issued Apr. 11, 1989, all of said patents being incorporated herein by reference. The spray bottle, or container can be any of the ones commonly used for containing hard surface cleaner detergent compositions. Examples of bottles are those in U.S. Design Pat. Nos.: 244,991, Weekman et al., issued Jul. 12, 1977; and 275,078, Wassergord et al., issued Aug. 14, 1984, said patents being incorporated herein by reference.

The spray means herein can also include those that incorporate a compatible propellant gas into the liquid and those that will foam even detergent compositions having a viscosity of less than about 15 cps. The device can also be one that can be adjusted to either give a liquid spray or a foam. The spray means herein are typically those that act upon a discrete amount of the composition itself, typically by means of a piston that displaces the composition and expels the composition through a nozzle to create a spray of thin liquid.

Preferred articles include the compositions herein that are suitable for use in the processes described herein, in a package that can provide a spray. Such articles are not widely marketed. This is surprising in view of the clear advantages for such products for use by individual consumers. The typical use involves treating individual items of produce, which would make preparation of a "bath" wasteful.

In a preferred process for using the products described herein, and especially those formulated to be used at full strength, the product is sprayed onto the food product to be cleaned, rubbed, rinsed and/or wiped off with a suitable clean material like cloth, sponge, a paper towel, etc.

Surprisingly, the compositions and processes described herein can provide effective disinfectancy/sanitization. In order to provide good kill of microorganisms, especially bacteria, one should use high concentrations and/or longer exposure times. Typically, the products should be used full strength and allowed to remain on the produce for at least about one minute, preferably at least about five minutes, and, for some microorganisms, even ten minutes may be required. Longer exposure times (i.e., the time that the bacteria are in contact with the product) give better antimicrobial benefits. The importance of time depends both on the pH of the product and on the formula concentration. At high pH ($\geq 11.5$) and high concentrations, antibacterial efficacy is achieved quickly. At lower pH values (pH$\leq 11$) and lower formula concentrations, a longer period of exposure time is required to achieve the same efficacy.

Higher pHs are also better, in general. This factor is important for the product's performance on the Gram negative bacteria, e.g., *Escherichia coli* and Pseudomonas species. Higher product pH's produce quicker and more complete kill. The opposite is true for the Gram positive bacteria, e.g., *Staphylococcus aureus*. Performance is equal to, or slightly better, as the pH is lowered from 11.5 to 9.5. However, this is only true when the formula contains oleic acid.

As stated above, higher formula concentrations (when done independently of pH) enhance the antimicrobial efficacy of the product. The presence of oleic acid is the key factor for the performance on Gram positive organisms like *S. aureus*, while the pH is probably a bigger factor for the Gram negative bacteria, e.g., *E. coli* and Pseudomonas species.

Packaging the products herein in a container with instructions for usage in terms of timing and avoidance of dilution in order to provide disinfectancy/sanitization, will help the individual consumer by providing information for proper usage in order to remove/kill microorganisms. It is a special advantage of the product that it can be used for this purpose at a time in the food production process where recontamination is minimized.

The compositions can also be used for cleaning (especially spot removal), disinfectancy, or sanitization, on non-food (i.e., any surface which is not used as food, even those which are not in contact with food), inanimate, household surfaces, especially those used in food production and other food-contacting surfaces (surfaces that come in contact with food). E.g., cutting boards, counter tops, utensils, dishes, colanders, sinks, sponges, towels, dish cloths, cloth napkins (serviettes), table cloths, and other surfaces that come in contact with food. It is desirable to disinfect/sanitize before the surfaces come in contact with the food, and is desirable to redisinfect/sanitize whenever the surfaces become recontaminated. The products herein, containing all GRAS ingredients, are perfect for this purpose. On hard surfaces, of course, the compositions can be removed, after sufficient time has elapsed, by rinsing or by absorption/wiping with an appropriate object, e.g., paper towel, sponge, squeegee, etc. Rinsing is still preferred.

The compositions of this invention can also be used to treat/clean other non-food inanimate household surfaces, such as fabrics, e.g., clothing, shoes, and shower curtains, especially those that are used by infants, especially toys, diapers (napkins), and bibs. The contaminated fabrics can be disinfected/sanitized, then rinsed off or washed, while minimizing the risk if the infant puts the fabric or other article in its mouth. The fabric can be treated totally, or by spot treatment, then the composition is removed, e.g., by rinsing/washing, absorbency, and/or mechanical force.

For fabrics, the pH of the compositions is preferably below about 11.5, more preferably below about 11.

For fabric and hard surfaces, the distribution of the compositions of this invention can be achieved by using a spray device, a roller, a pad, etc., or dipping in a "bath" of said compositions. Spraying is a preferred method.

All parts, percentages, and ratios herein are "by weight" unless otherwise stated. All number values are approximate unless otherwise stated.

The following Examples illustrate the compositions and processes of this invention, but are not intended to be limiting thereof The exemplified basic liquid compositions can be prepared at pH 9.5–12.5 by dissolving the ingredients in water or water-ethanol using conventional mixing apparatus. In a convenient mode, water is placed in a mixing vessel. Potassium hydroxide, the ortho-phosphoric acid, any citric acid, any bicarbonate, glycerine (processing aid), and any ethanol are added in the named sequence, with stirring. The oleic acid is added with high shear and stirring is continued. The PEG (which can conveniently be predispersed in water) is then added. The optional perfume ingredients can be added any time after the oleic acid has been dissolved in the mixture.

EXAMPLE 1

| Product Ingredient | Control level % | A level % | B level % | Water level % |
|---|---|---|---|---|
| Water | 90.93 | 90.90 | 88.20 | 100.00 |
| KOH | 1.33 | 1.36 | 3.06 | — |
| Ethanol | 2.00 | 2.00 | 2.00 | — |
| Glycerin | 2.00 | 2.00 | 2.00 | — |
| Oleic acid | 2.64 | 2.64 | 2.64 | — |
| Sodium Bicarbonate | 0.55 | 0.55 | 0.55 | — |
| Phosphoric Acid | — | — | 1.00 | — |
| Citric acid | 0.52 | 0.52 | 0.52 | — |
| Essence | 0.03 | 0.03 | 0.03 | — |
| Neat pH | 11.5 | 12.0 | 12.2 | ~7.5 |

Glass flasks are coated with AP-40 shellac and stress cured for 24 hours @140 F. The flasks at room temperature are then washed with ~5 grams 5 squirts of a Calmar #TS-800 sprayer) of the respective products with a 10 sec. rub, followed immediately with a water rinse, and allowed to dry. The % Wax removal is determined gravimetrically.

| % Wax Removal | Control 14%; A 9%; B 38%; and Water 0%. |
|---|---|

Note:
A vs. B shows a benefit for phosphoric acid addition at similar pH.

EXAMPLE 2

| Product Ingredient | Control level % | A level % | B level % | C level % | Water reference level % |
|---|---|---|---|---|---|
| Water | 90.93 | 88.08 | 88.05 | 88.05 | 100.00 |
| KOH | 1.33 | 3.06* | 3.06* | 3.06 | — |
| Ethanol | 2.00 | 2.00 | 2.00 | 2.00 | — |
| Glycerin | 2.00 | 2.00 | 2.00 | 2.00 | — |
| Oleic acid | 2.64 | 2.64 | 2.64 | 2.64 | — |
| Sodium Bicarbonate | 0.55 | 0.55 | 0.55 | 0.55 | — |
| Phosphoric Acid | — | 1.00 | 1.00 | 1.00 | — |
| Citric acid | 0.52 | 0.52 | 0.52 | 0.52 | — |
| Essence | 0.03 | 0.03 | 0.03 | 0.03 | — |
| PEG 3350 | — | 0.12 | 0.15 | 0.15 | 0 |
| Neat pH | 11.5 | 12.6 | 12.0 | 11.5 | ~7.5 |

*Target KOH usage. Very small amount of additional KOH, replacing water, used to adjust to final pH.

Using varying wax, curing, rub time and flask temperature, the above compositions were used to clean in a manner similar to EXAMPLE 1, followed by a determination of the percentage of wax removed. The test conditions and results are as follows.

| Wax/Curing/Rub time/flask Temp. | % Wax Removal | | | | |
| --- | --- | --- | --- | --- | --- |
| | Control | A | B | C | Water |
| Shellac/60 min. @ 75° C./ 10 sec./room temp. | 51 | 97 | 73 | 82 | 9 |
| Carnauba/60 min. @ 43° C./ 10 sec./room temp. | 64 | 82 | 75 | 73 | 5 |
| Shellac/60 min. @ 75° C./20 sec./40 F | 57 | 97 | 96 | 97 | 7 |
| Shellac/30 min. @ 93° C./ 20 sec./room temp. | 50 | 98 | 61 | 65 | 3 |

The compositions of Examples 1 and 2 are prepared by adding oleic acid to a mixture of water, KOH, citric acid, phosphoric acid (if used), sodium bicarbonate, glycerin, and ethanol. The PEG 3350 (if used) and essence are added last.

EXAMPLE 3

| Product Ingredient | A level % | B level % | C level % | D level % |
| --- | --- | --- | --- | --- |
| Water | 89.79 | 90.63 | 88.068 | 88.91 |
| KOH | 2.12 | 1.28 | 2.842 | 2.00 |
| Ethanol | 2.00 | 2.00 | 2.00 | 2.00 |
| Glycerin | 2.00 | 2.00 | 2.00 | 2.00 |
| Oleic acid | 2.643 | 2.643 | 2.643 | 2.643 |
| Sodium Bicarbonate | 0.547 | 0.547 | 0.547 | 0.547 |
| Phosphoric Acid | 0.00 | 0.00 | 1.00 | 1.00 |
| Citric acid | 0.52 | 0.52 | 0.52 | 0.52 |
| Essence | 0.03 | 0.03 | 0.03 | 0.03 |
| PEG 3350 | .350 | .350 | .350 | .350 |
| Neat pH | 11.5 | 10.5 | 11.5 | 10.5 |

The above formulas are evaluated for ability to kill various standard microorganisms. Minor adjustments of the pH of the formulas were done immediately prior to antimicrobial testing to give the above neat pH values. The formulas kill standard microorganisms effectively, and the formulas containing phosphoric acid are better, especially at lower pH. The amount of time required for control of microorganisms is more than would ordinarily be provided by a normal cleaning operation. Therefore, it is important to package the product in a container with instructions for allowing sufficient time for effective kill to take place.

EXAMPLE 4

| Product Ingredients | A Level % | B Level % |
| --- | --- | --- |
| Oleic Acid | 2.64 | 2.20 |
| Sodium Bicarbonate | 0.55 | 0.55 |
| Phosphoric Acid | 1.00 | — |
| Citric Acid | 0.52 | 0.52 |
| EDTA, Sodium Salt | 0.05 | 0.10 |
| GRAS Perfume | 0.05 | 0.08 |
| PEG 3350 | 2.00 | — |
| KOH | * | ** |
| Ethanol | 2.00 | 2.00 |
| Water | Balance | Balance |

*Amount sufficient to attain a pH of about 11.
**Amount sufficient to attain a pH of about 10.5.

Each of the Compositions of Examples 1 Control, 4A, and 4B is used to spray on a contaminated Formica™ kitchen countertop, left on the surface for about 10 min., then rinsed off to provide a sanitizing benefit.

Each of the Compositions of Examples 2 Control, 4A, or 4B is used to spray on a contaminated area of a 50/50 poly/cotton shirt, left on the fabric for about 10 min., then the treated shirt is added to a laundry load to be washed in a normal fashion in an automatic washer with a commercial detergent, to provide a sanitizing benefit.

EXAMPLE 5

| Ingredient | Wt % |
| --- | --- |
| Water | 73.26 |
| PEG 3350 | 0.79 |
| KOH | 5.70 |
| Ethanol | 6.00 |
| Glycerin | 3.00 |
| Oleic acid | 7.90 |
| Sodium bicarbonate | 1.60 |
| Phosphoric acid | 1.00 |
| Citric acid | 1.56 |
| Essence (Grapefruit oil) | 0.09 |

The concentrated composition in Example 5 can be mixed, for example, with distilled water at 1 part product to 2 parts water until uniformly mixed and then used as a lower active liquid.

EXAMPLE 6

| Ingredient | Wt % |
| --- | --- |
| Tri-Potassium Phosphate (TKP) | 48.8 |
| Potassium Citrate | 10.2 |
| PEG 3350 | 4.3 |
| Potassium Oleate | 36.7 | the anhydrous dry composition in Example 6 can be mixed, for example, with distilled water at 1 part product to 11 parts water until uniformly dissolved/mixed and then used in a liquid form.

What is claimed is:

1. An article of commerce comprising a container containing an aqueous cleaning solution which cleans and reduces a significant number of microorganisms on produce when allowed to remain in contact with the produce for at least about one minute and comprises:
   (a) from 0.5% to about 15% by weight of $C_8$–$C_{18}$ fatty acid;
   (b) optionally, from about 0.1% to about 4% by weight of nonionic surfactant;
   (c) optionally, from about 0.1% to about 4% by weight of organic polycarboxylic acid;
   (d) optionally, up to about 0.2% by weight of a base-stable anionic surfactant;
   (e) optionally, a toxicologically-acceptable basic buffer;
   (f) optionally, a toxicologically-acceptable preservative;
   (g) optionally, from about 0.05% to about 10% by weight of phosphoric acid; and
   (h) the balance comprising an aqueous carrier containing water and, optionally, low molecular weight, toxicologically-acceptable organic solvent;
wherein said aqueous solution has a pH of more than 10.5, and where said container has instructions for cleaning and reducing a significant number of microorganisms on produce comprising the instruction to apply the solution to the surface of produce and to allow the solution to remain in contact for at least about one minute.

2. The article of commerce of claim 1 wherein said aqueous cleaning solution comprises:
   (a) from about 0.5% to about 10% by weight of oleic acid;
   (b) optionally, from about 0.3% to about 1% by weight of nonionic surfactant;
   (c) optionally, from about 0.2% to about 4% by weight of organic polycarboxylic acid;
   (d) optionally, up to about 0.2% by weight of a base-stable anionic surfactant;
   (e) optionally, a toxicologically-acceptable basic buffer;
   (f) optionally, a toxicologically-acceptable preservative;
   (g) optionally, from about 0.1% to about 5% by weight of phosphoric acid; and
   (h) the balance comprising an aqueous carrier selected from water and, optionally, low molecular weight, toxicologically-acceptable organic solvent;
wherein said aqueous solution has a pH of from 11 to about 12.5, and where said container has instructions for treating produce comprising the instruction to apply the solution to the surface of produce and to allow the solution to remain in contact for at least about five minutes.

3. The article of claim 2 wherein said container is a spray container, suitable for use by an individual to clean produce.

4. The article of claim 1 wherein said container is a spray container, suitable for use by an individual to clean produce.

5. The article of claim 2 wherein said container is a spray container, suitable for use by an individual to clean produce and wherein all of the ingredients of said solution are GRAS, wherein there is at least 0.5% by weight of detergent.

* * * * *